(12) United States Patent
Purcell et al.

(10) Patent No.: US 7,886,745 B2
(45) Date of Patent: *Feb. 15, 2011

(54) SELF-FITTING DEVICE FOR LOCATION IN AN EAR CANAL

(75) Inventors: Ricky Wayne Purcell, Alpharetta, GA (US); Scott M. Belliveau, Plainfield, IL (US); Thomas A. Wozny, Westchester, IL (US); Kenneth Michael Ross, Chicago, IL (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 152 days.

This patent is subject to a terminal disclaimer.

(21) Appl. No.: 12/217,041

(22) Filed: Jun. 30, 2008

(65) Prior Publication Data

US 2009/0320858 A1    Dec. 31, 2009

(51) Int. Cl.
    A61F 11/00    (2006.01)
    H04R 25/02    (2006.01)
    H04R 25/00    (2006.01)

(52) U.S. Cl. .................. 128/864; 181/130; 181/135; 381/328; 381/329; 381/322

(58) Field of Classification Search ......... 128/864–868; 181/135, 130; 623/10; 381/322, 328–329, 381/72
See application file for complete search history.

(56) References Cited

U.S. PATENT DOCUMENTS

| 2,246,736 A | 6/1941 | Knudsen |
| 2,824,558 A | 2/1958 | Michael et al. |
| 2,850,012 A | 9/1958 | Becker |
| 2,876,767 A * | 3/1959 | Wasserman ............. 128/865 |
| 3,123,069 A | 3/1964 | Laisne et al. |
| 3,736,929 A | 6/1973 | Mills |
| 4,060,080 A | 11/1977 | Akiyama |
| 4,133,984 A | 1/1979 | Akiyama |
| 4,582,053 A | 4/1986 | Wilson |
| 4,913,165 A | 4/1990 | Fishgoyt |

(Continued)

FOREIGN PATENT DOCUMENTS

EP    1276443 B1    3/2006

(Continued)

OTHER PUBLICATIONS

Patent Cooperation Treaty Search Report from the International Search Authority, International Application No. PCT/IB2009/052714 dated Feb. 23, 2010.

*Primary Examiner*—Patricia M Bianco
*Assistant Examiner*—Tarla R Patel
(74) *Attorney, Agent, or Firm*—Michael J. Bendel; Nathan P. Hendon (57) ABSTRACT

A self-fitting device for location in an ear canal. The device includes a body having a body ear end, an opposite body user end, and a shaft extending from the ear end to the user end. A resilient bladder is joined with the body ear end and a chamber is defined inside the resilient bladder where the chamber is in communication with the shaft and the resilient bladder has a wall portion and is deformable from an at-rest position to an in-ear position. The resilient bladder has a variable strength profile in the wall portion of the bladder.

17 Claims, 7 Drawing Sheets

U.S. PATENT DOCUMENTS

| | | | |
|---|---|---|---|
| 5,293,008 A * | 3/1994 | Danielsen | 181/135 |
| D364,455 S | 11/1995 | Krause | |
| D366,313 S | 1/1996 | Krause | |
| D366,696 S | 1/1996 | Krause | |
| 5,483,027 A | 1/1996 | Krause | |
| 6,006,857 A * | 12/1999 | Leight et al. | 181/135 |
| 6,256,396 B1 * | 7/2001 | Cushman | 181/135 |
| 6,942,696 B1 | 9/2005 | White et al. | |
| 7,362,875 B2 * | 4/2008 | Saxton et al. | 381/322 |
| 2008/0144871 A1 * | 6/2008 | Purcell et al. | 381/329 |
| 2008/0264428 A1 * | 10/2008 | Purcell et al. | 128/864 |
| 2009/0173353 A1 | 7/2009 | Purcell et al. | |
| 2009/0320859 A1 * | 12/2009 | Purcell et al. | 128/864 |

FOREIGN PATENT DOCUMENTS

| | | |
|---|---|---|
| EP | 1 653 776 A2 | 5/2006 |
| GB | 1 423 194 A | 1/1976 |
| GB | 2 323 295 A | 9/1998 |
| JP | 06-343659 A | 12/1994 |
| JP | 10-094615 A | 4/1998 |
| JP | 2002-000637 A | 1/2002 |
| WO | WO 98/25558 A1 | 6/1998 |
| WO | WO 2004/100608 A2 | 11/2004 |
| WO | WO 2008/075221 A1 | 6/2008 |

* cited by examiner

SELF-FITTING DEVICE FOR LOCATION IN AN EAR CANAL

BACKGROUND OF THE INVENTION

The present invention relates generally to devices for location in an ear canal, and more particularly to such devices being self-fitting and used for sound optimization such as noise reduction and/or acoustic enhancement.

The need for adequate hearing protection in high noise environments has long been recognized among those concerned with health and safety issues, and much effort has gone into providing such protection. However, most experts in this field would acknowledge that there is still room for improvement. Protective devices have proliferated yet remained less than perfect in performance. Workers in high noise environments who should use these devices often do not, or use them only under duress from their employers. Individuals that work in high noise environments rarely understand that the effects of high noise exposure are not limited to the moment but are cumulative as well. The lack of worker compliance with safety rules is exacerbated by the fact that currently available hearing protection devices are often uncomfortable, clumsy to use, and/or perform poorly. Fortunately, as hearing protection devices become more comfortable and perform better, worker compliance with their use should also improve.

For example, existing disposable foam ear plugs are uncomfortable for wearers with small ear canals, are difficult to properly insert, must be completely removed if noise reduction is unwanted for a brief period (e.g. conversation), and/or cause discomfort by creating a vacuum in the ear canal during removal. Common disposable foam ear plugs require the user to compress the volume of the plug and insert it into the ear canal where it then attempts to re-expand. This method can cause discomfort for people with small ear canals in that the more compressed the ear plug, the greater its exerted force toward re-expansion. Further, existing disposable foam ear plugs require the user to roll the foam between their fingers to compress the foam to a sufficient size for proper insertion. If this step is not done, or is insufficiently done, the ear plug is often inserted improperly so as to not provide optimal protection. Also, if the user has dirty hands when compressing the ear plug, dirt and/or germs are then put into the ear canal with the inserted ear plug.

Further, existing disposable foam ear plugs must be completely removed if the user needs increased use of their hearing faculties for a brief period such as engaging in conversation with a coworker. This could lead to improper reinsertion if the earplugs are removed or misunderstanding of potentially important information if not removed. Also, existing disposable foam ear plugs are sealed against the wall of the ear canal in use and at the moment of removal. This causes a vacuum within the ear canal as the ear plugs are removed, and makes removal difficult and/or uncomfortable. And, existing foam ear plugs are often designed for one time use.

Accordingly, while various types of in-ear devices exist in the art, there remains a need for an in-ear device that helps overcome one or more of the aforementioned problems. The applicants have surprisingly invented such a device, as discussed further herein.

SUMMARY OF THE INVENTION

Various definitions used throughout the specification and claims are provided first, followed by a description of various aspects of the invention.

As used herein, "resilient" means that property of a material or composite material that permits it to be deformed in size and/or shape and then recover at least about 80% of its original size and shape no later than two minutes after removal of the force causing the deformation.

As used herein, "non-resilient" means the opposite of resilient.

In one aspect of the present invention, there is provided a self-fitting device for location in an ear canal. The device includes a body having a body ear end, an opposite body user end, and a shaft extending from the ear end to the user end. A resilient bladder is joined with the body ear end and a chamber is defined inside the resilient bladder where the chamber is in communication with the shaft and the resilient bladder has a wall portion and is deformable from an at-rest position to an in-ear position. The resilient bladder has a variable strength profile in the wall portion of the bladder.

In another aspect of the present invention, there is provided a self-fitting device for location in an ear canal. The device includes a body having a body ear end, an opposite body user end, and a shaft extending from the ear end to the user end. A resilient bladder is joined with the body ear end and a chamber is defined inside the resilient bladder where the chamber is in communication with the shaft and the resilient bladder has a wall portion and is deformable from an at-rest position to an in-ear position. The resilient bladder includes a plurality of relief zones located in an inside portion of the wall portion of the bladder. An elongate plunger is located in the shaft, the elongate plunger having a plunger user end extending out of the shaft and away from the body ear end and an opposite plunger ear end in communication with the resilient bladder. The elongate plunger actuates between the at-rest position and an insertion position to assist the resilient bladder in being deformed from the at-rest position to the in-ear position. The resilient bladder has a first cross-sectional area in the at-rest position and a second cross-sectional area in the in-ear position, and the first cross-sectional area is greater than the second cross-sectional area.

In still another aspect of the present invention, there is provided a self-fitting device for location in an ear canal. The device includes a body having a body ear end and an opposite body user end and a body cross-section with a body cross-section width. A resilient bladder is joined with the body and has a wall portion that is deformable from an at-rest position to an in-ear position. The resilient bladder also has a bladder cross-section where the bladder cross-section has a bladder cross-section width that is greater than the body cross-section width. The resilient bladder has a variable strength profile in the wall portion of the bladder.

Other features of the invention relate to particular configurations of the resilient bladder per se and when in the various at-rest, in-ear and insertions positions; and, particular structures for deforming the bladder between these positions.

Still other features of the invention will be in part apparent and in part pointed out hereinafter as well as better understood by practice of the invention. It is to be understood that both the foregoing general description and the following detailed description are exemplary and are intended to provide further explanation of the invention claimed. The accompanying drawings, which are incorporated in and constitute part of this specification, are included to illustrate and provide a further understanding of the self-fitting device for location in an ear canal that is the present invention.

BRIEF DESCRIPTION OF THE DRAWINGS

Corresponding reference characters indicate corresponding parts throughout the drawings.

DETAILED DESCRIPTION

Referring now to the drawings and in particular FIGS. 1-6 for example, there is depicted a self-fitting device 10 for location in an ear canal 12. Particularly in FIG. 4-6, there is seen outer ear 13 joined to the portion of the ear canal 12 through which the device 10 is inserted for use, and where the ear drum (not seen) is located at the other end of the ear canal spaced from the device when inserted into the ear canal. Device 10 includes a body 20, a resilient bladder 70 and an elongate plunger 40. Body 20 includes a body ear end 22 and an opposite body user end 24. A shaft 26 extends from the ear end to the user end. More advantageously, though not required, the shaft can have closed sides and the elongate plunger extends through and between the ear end and the user end.

Resilient bladder 70 can be joined with the body ear end 22 of body 20. For example, these two parts could be formed together of one material, or formed of separate materials that are sequentially formed together, or formed separately and then joined together by any conventional means (e.g., adhesive, chemical or heat or other similarly resulting mechanical bonded relationship). A chamber 72 (seen best in FIGS. 8-13) can be defined inside the resilient bladder. Chamber 72 is in communication with shaft 26 when bladder 70 is joined with body 20.

Also referring to FIGS. 8-9 and 11-12, elongate plunger 40 is located in shaft 26. The elongate plunger has a plunger user end 44 which extends out of the shaft, when the plunger is located inside the shaft, and away from the body ear end 22. Plunger 40 also has an opposite plunger ear end 42 able to be in communication with the resilient bladder, when the plunger is located inside the shaft. For example, the communication may be via a pressure type relationship and not direct contact of plunger with bladder, or plunger ear end 42 may engage the resilient bladder at least when the resilient bladder is deformed. Still further, the plunger ear end 42 may be joined with the resilient bladder temporarily or permanently, once the bladder is assembled with the body 10.

Figure 10:
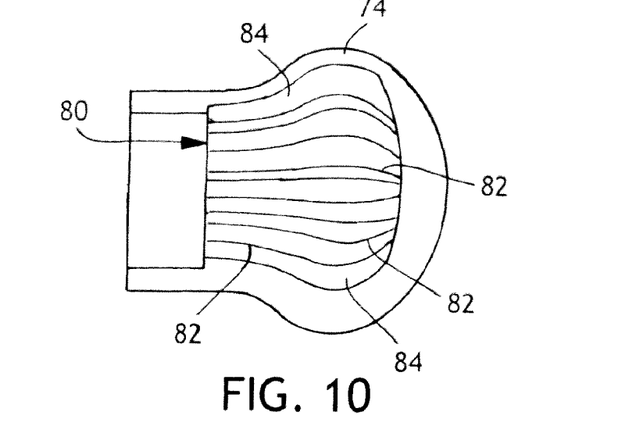
FIG. 10 is a cross-sectional side view of a portion of the present invention in the at-rest position, and without the elongate plunger.

The resilient bladder 70 is deformable between an at-rest position (FIGS. 1, 4, 7, and 10-13) to an in-ear position (FIGS. 3 and 6) to an insertion position (FIGS. 2 and 5) such that the resilient bladder has a first cross-sectional area 50 in the at-rest position, a second cross-sectional area 52 in the in-ear position and optionally has a third cross-sectional area 54 in the insertion position. First cross-sectional area 50 is greater than second cross-sectional area 52, and second cross-sectional area 52 can be greater than optional third cross-sectional area 54. The cross-sectional area is determined using the plane orthogonal to the length (longest dimension) of device 10 and parallel to respective area lines 50, 52, 54, and then measuring the largest area of the portion of the resilient bladder that would engage (at-rest and insertion positions) or does engage (in-ear position) the inside of the ear canal, taking view 56 (FIGS. 10 and 14). It is noted that the shapes of the bladder seen in FIGS. 1-6 are illustrative of the relative differences between at-rest, optionally insertion, and in-ear positions, but such shapes are not so limited (e.g., the bladder in FIGS. 2 and 5 may be more or less bulbous but would be less bulbous than that in FIGS. 1 and 4, and may be less bulbous than that in FIGS. 3 and 6 but need not be so).

Referring to FIGS. 10-17, other features of bladder 70 concern a wall portion 74 that is deformable from the at-rest position to the in-ear position. Such wall portion 74 can have a variable strength profile in the wall portion of the bladder. For example, and without be limited to a theory of understanding, this adds flexibility and/or compliance to the bladder during the insertion process, and/or such flexibility and compliance adding comfort when the device is in the in-ear position, particularly for longer term use in the user's ear.

Figure 11:
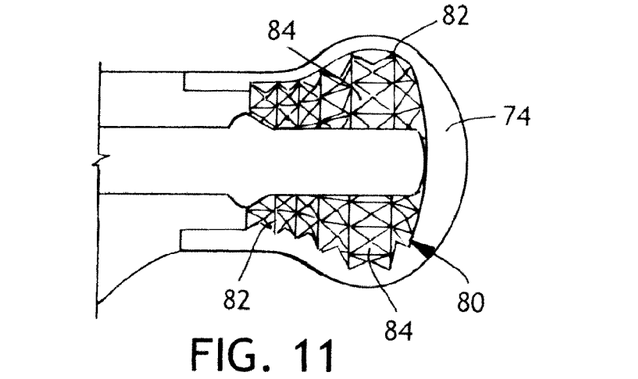
FIG. 11 is a cross-sectional side view of a portion of the present invention in the at-rest position, depicting an alternate bladder configuration.
Figure 12:
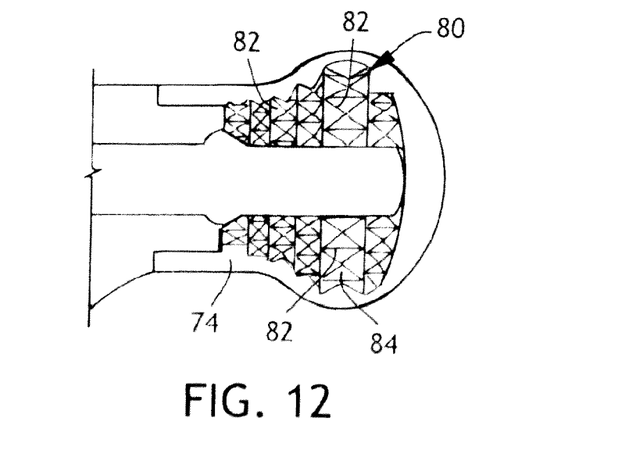
FIG. 12 is a cross-sectional side view of a portion of the present invention in the at-rest position, depicting yet another bladder configuration.
Figure 15:
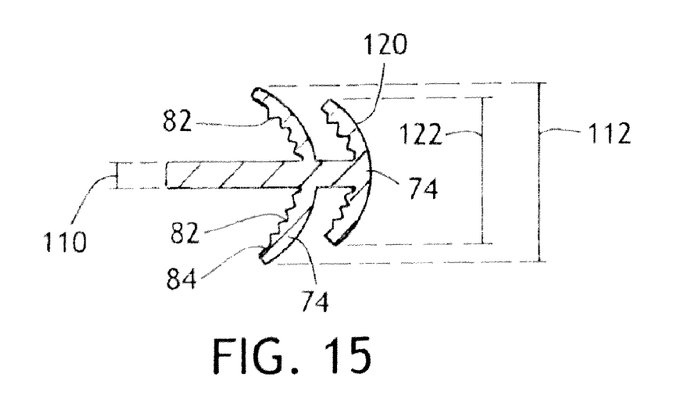
FIG. 15 is a cross-sectional side view of still another embodiment of the present invention, in the at-rest position.
Figure 16:
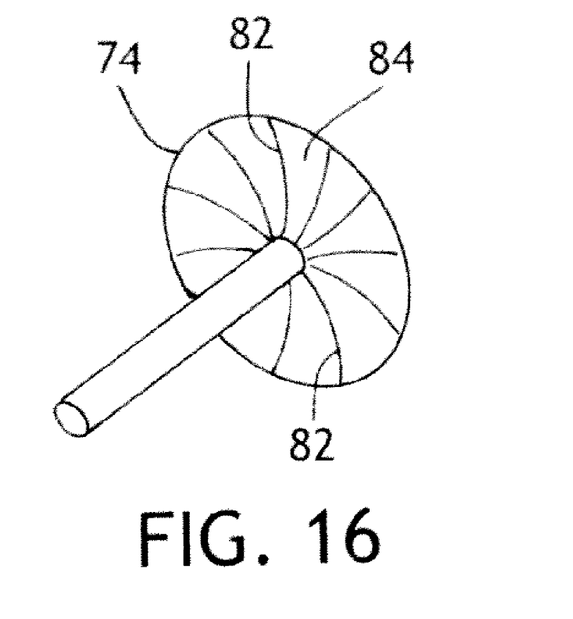
FIG. 16 is a cross-sectional side view of yet another embodiment of the present invention, in the at-rest position.
Figure 17:
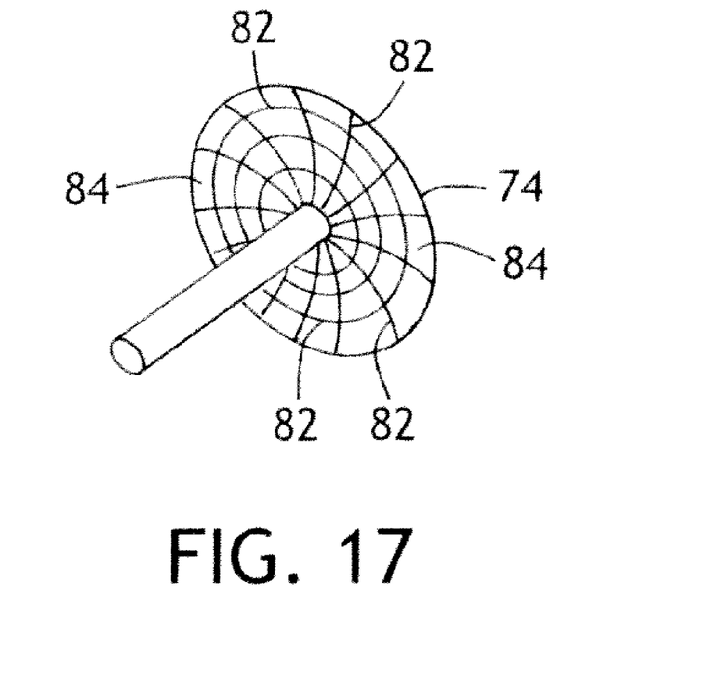
FIG. 17 is a cross-sectional side view of yet another embodiment of the present invention, in the at-rest position.

The variable strength profile can be provided in a variety of ways. For example, a plurality of relief zones can be located in an inside portion 80 of the wall portion of the bladder. The relief zones may be grooves 82 located in an inside surface 84 of the wall portion of the bladder. The grooves may be axial grooves, as best seen in FIGS. 10 and 15. The grooves may be radial grooves, as seen in FIG. 16, and in combination with axial grooves in FIGS. 11-12 and 17. The grooves may be a combination of such grooves to form a criss-cross pattern of grooves, as seen in FIGS. 11-12 and 17. Still further, the relief zones may be a network of peaks and valleys in the wall portion of the bladder, for example the inside surface as seen in FIGS. 10-12 and 15-17. Further, such a network may be an aligned pattern of the peaks and valleys, as seen in FIGS. 11 and 17 (as opposed to the offset pattern seen in FIG. 12).

Figure 13:
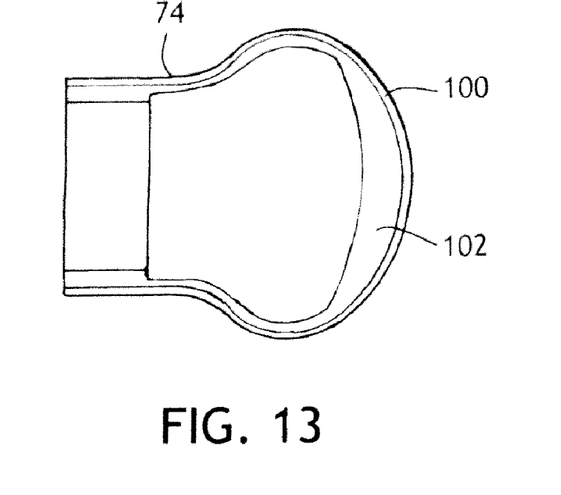
FIG. 13 is a cross-sectional side view of a portion of the present invention in the at-rest position, depicting still another bladder configuration.
Figure 14:
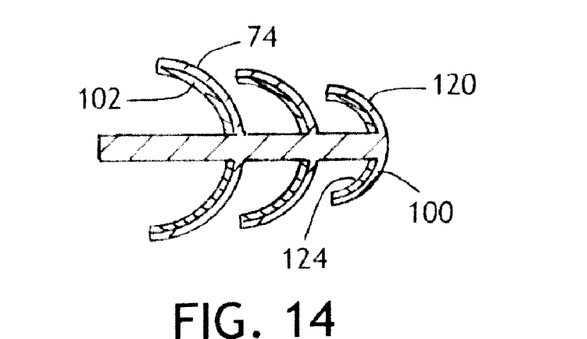
FIG. 14 is a cross-sectional side view of an another embodiment of the present invention, in the at-rest position.

Referring principally to FIGS. 13-14, the advantages of the variable strength profile may be achieved, alternatively or additionally to those already presented, by the resilient bladder being formed of a first layer 100 overlying a second layer 102. And, the first layer having a first durometer and the second layer having a second durometer, with the first durometer being different than the second durometer. Advantageously, the first durometer can be greater than the second durometer. Still more advantageous, the durometer of the first layer can be in the range of 20 Shore A thru 70 Shore A, and the durometer of the second layer can be in the range of 20 Shore OO thru 40 Shore A. As a multi-layer material, while each layer has its individual durometer, together the layers behave as though they are a material with a durometer in the range of 20 to 40 Shore A. And, this can be further considered within a range of total thickness for the multi-layer material of the bladder being from 0.25 millimeters to 2 millimeters, and more advantageously 0.5 millimeters to 1.5 millimeters.

Elongate plunger 40 actuates between the at-rest position and the insertion position to assist resilient bladder 70 to be deformed from the at-rest position into the in-ear position, and optionally into the insertion position before the device is located in the ear canal. Elongate plunger 40 can be configured such that at least 50% of its length 46, including the plunger ear end 42, travels only through movement that is parallel to shaft 26. This configuration and more parallel movement can provide an efficient and effective force for easily actuating plunger 40, and in turn, bladder 70. Building on this advantage, in particular suitable aspects of increasing advantage, though not required, the at least 50% of length 46 may be at least 60%, at least 70%, at least 80%, at least 90%, or all of the length of the elongate plunger including the plunger ear end. Still further, additionally or alternatively, the elongate plunger may be actuated by a force 60 applied in a direction that is substantially parallel to the shaft, as in FIGS. 1-9. For example, the force may be applied to the plunger user end 44 of the elongate plunger.

While not required, it may be advantageous for enhanced sound reduction to have a fluid (e.g., gas, liquid, gel or similarly functioning material(s)) in chamber 72 of resilient bladder 70. As such, the fluid would be sealed from an environment 16 outside bladder 70. Alternatively, and generally, chamber 72 need not be sealed from the environment 16. The figures showing device 10 in an assembled configuration enable chamber 72 to be sealed or unsealed, all dependent upon the nature of the seal between the bladder 70 and body ear end 22 and a sealed (yet movable) relationship between shaft 26 and plunger 40 which actuates inside the shaft to operate the bladder.

While not required, the invention may be advantageous for sound enhancement, e.g., not only taking advantage of sound reduction capabilities but also hearing aid like capabilities. In this way, device 10 can be configured (not shown) to locate a microphone or the like in device 10 and help bring desired sound into the ear canal and/or locate a microphone in the ear canal better, e.g., via shaft 26 in communication with bladder 70.

The resilient bladder may be made of a homogeneous material or a composite material, and may include one or more layers, and two layers of different durometer as noted above. When formed as a homogeneous material, bladder 70 may be made of a polyurethane foam with a "skin" formed on the outside. When formed as a composite or multi-layer material, bladder 70 could have an inner foam layer and an outer higher durometer layer may be made of foam or another flexible material. It may be made from a flexible material that is injection or blow moldable into a bulb that does not permanently deform when stressed by squeezing. Examples could be polyurethane, polyvinylchloride, santoprene, polyethylene, or polypropylene, in a foam or non-foam form.

Figure 1:
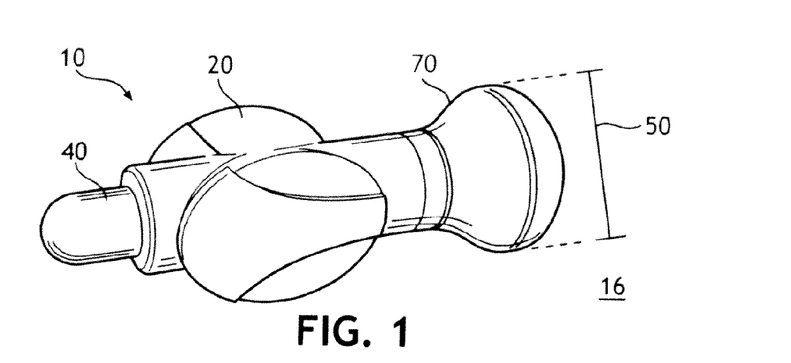
FIG. 1 is a perspective view of the present invention in the at-rest position.
Figure 2:
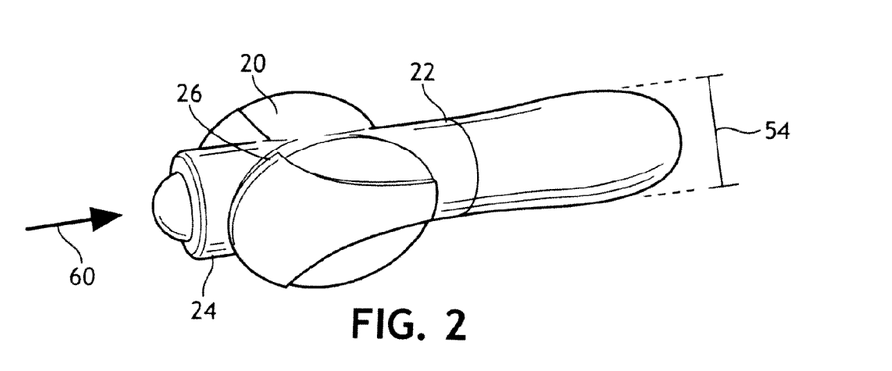
FIG. 2 is a perspective view of the device in FIG. 1, but now in the insertion position.
Figure 3:
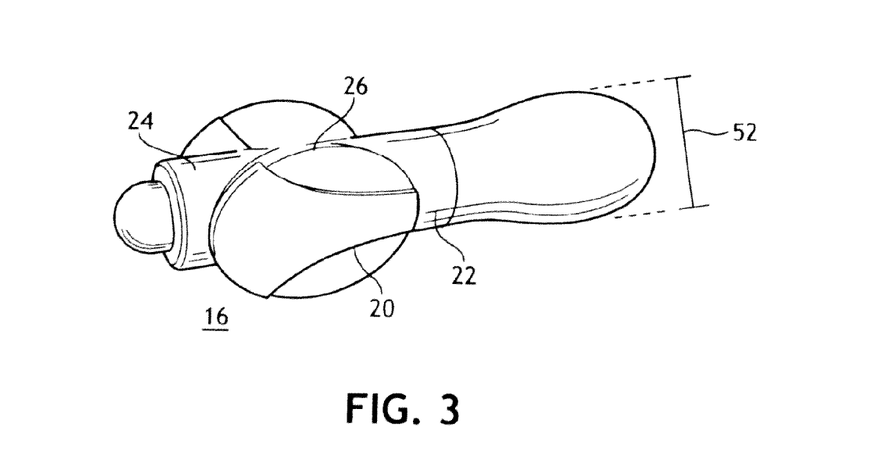
FIG. 3 is a is perspective view of the device in FIG. 1, but now in the in-ear position.
Figure 4:
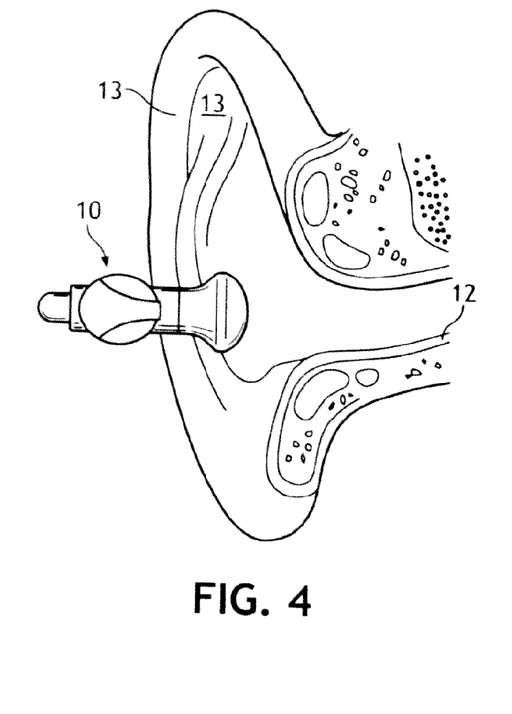
FIG. 4 is a perspective view of the device in FIG. 1, as it is approaching and being made ready for insertion in an ear canal.
Figure 5:
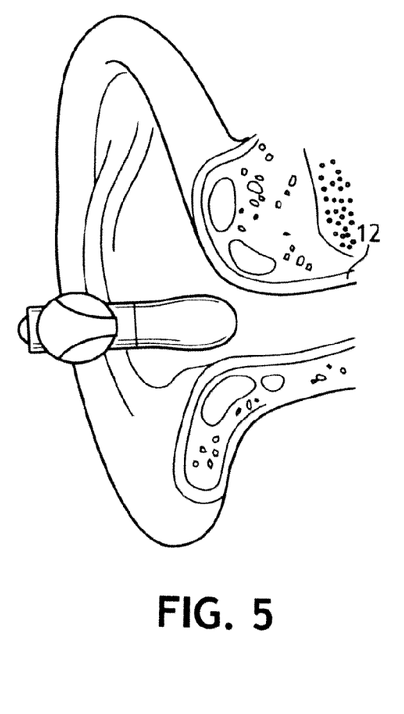
FIG. 5 is a perspective view of the device in FIG. 4, as it is being inserted in the ear canal, with the device in the insertion position.
Figure 6:
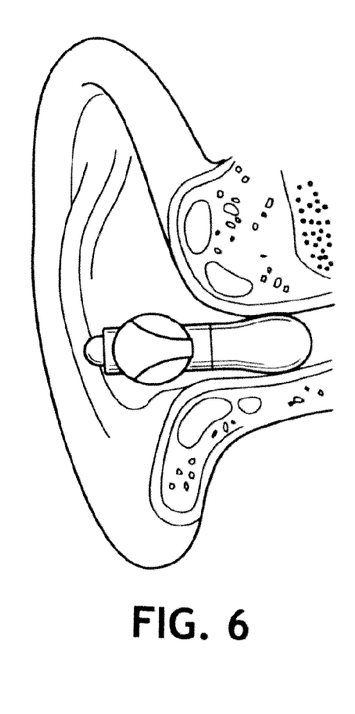
FIG. 6 is a perspective view of the device in FIG. 5, as it is now fully inserted in the ear canal and with the device in the in-ear position.
Figure 7:
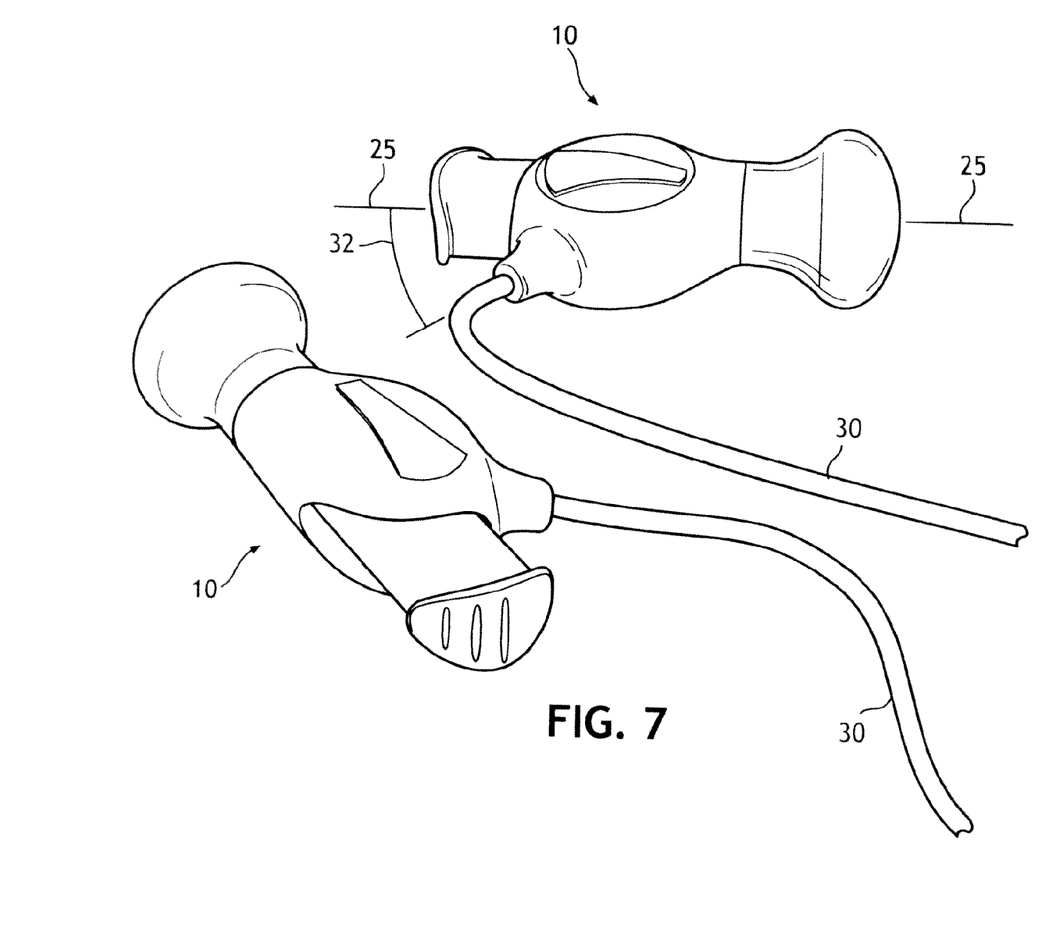
FIG. 7 is a perspective view of a pair of devices of the present invention in the at-rest position.

Additional features relate to the plunger and bladder configurations, as well as others. In FIG. 7 is a pair of devices 10, and they are connected together by a lanyard 30 or other similar connection means for a variety of reasons, e.g., easy location when not in an ear canal, to help remove from the ear canal, to keep from falling into a user's work space, or the like.

Referring to FIG. 7, device 10 may include a lanyard 30 joined with body 20. Lanyard 30 may, advantageously though not required, be positioned such that an acute angle 32 between an axis of lanyard 30 and the longitudinal axis 25 of shaft 26 is formed in the range of 80 degrees to 10 degrees. More advantageously in this regard, if desired, the acute angle may be in the range of 65 degrees to 35 degrees, and still more advantageously, if desired, acute angle 32 may be in the range of 50 degrees to 40 degrees.

Figure 8:
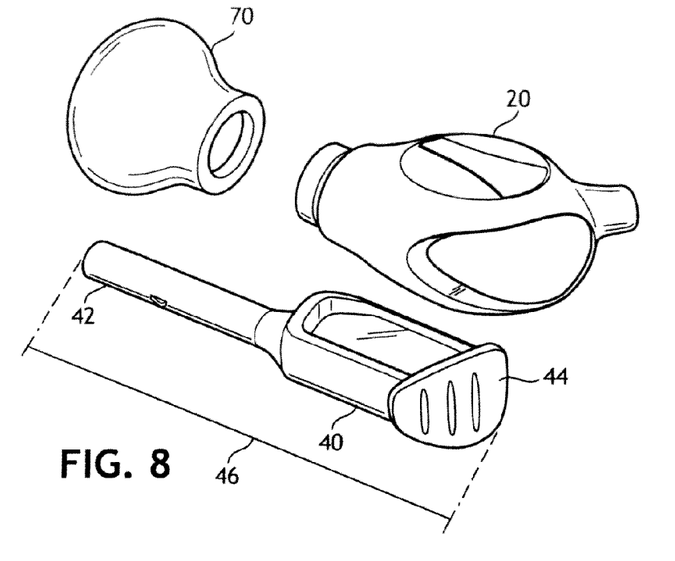
FIG. 8 is an exploded perspective view of one of the devices in FIG. 7.
Figure 9:
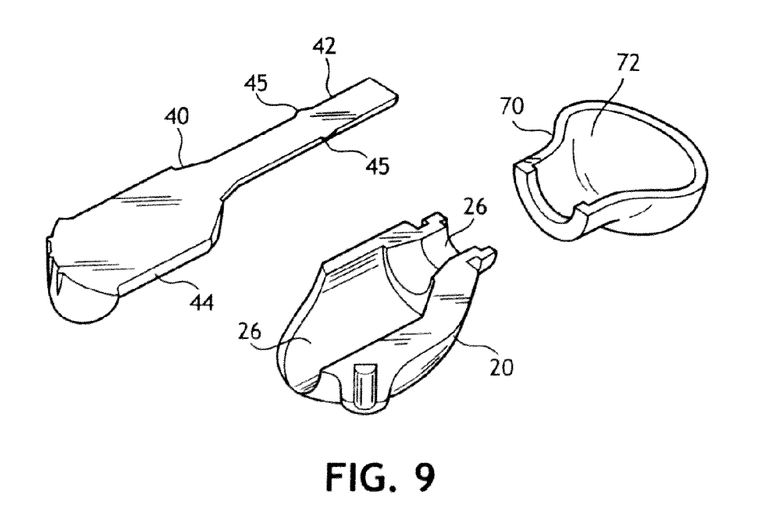
FIG. 9 is a cross-sectional side view of the parts of the device in FIG. 8.

As seen in FIGS. 8 and 9, plunger 40 may have a detent 45 to locate and/or maintain the plunger in the shaft 26 once located in shaft 26. Detent 45 may sit against seat 27 when the device is in the at-rest position, as seen in FIGS. 11-12.

In other aspects of the invention there is provided an ear canal self-fitting device method. The method includes providing the body 20 having body ear end 22 and opposite body user end 24 and shaft 26 extending from the ear end to the user end. The method also includes locating elongate plunger 40 in the shaft with the elongate plunger having plunger user end 44 extending out of the shaft and away from the body ear end and the plunger having opposite plunger ear end 42. The method further includes joining resilient bladder 70 with the body ear end of the elongate body and over the plunger ear end. In this way, the plunger ear end can be in communication with the resilient bladder, and the resilient bladder is deformable from the at-rest position to the in-ear position and optionally to the insertion position, such that the resilient bladder has first cross-sectional area 50 in the at-rest position, second cross-sectional area 52 in the in-ear position and optional third cross-sectional area 54 in the insertion position, with first cross-sectional area 50 being greater than second cross-sectional area 52 and second cross-sectional area 52 optionally being greater than the third cross-sectional area 54. The method still further includes actuating elongate plunger 40 between the at-rest position and the insertion position to assist the resilient bladder 70 in being deformed from the at-rest position, optionally to the insertion position before the device is located in ear canal 12, to the in-ear position. The method can further include limiting at least 50% of the length 46 of the elongate plunger including the plunger ear end, to traveling only through movement that is parallel to shaft 26 when actuating the elongate plunger. Alternatively to, or in addition to, the previous step, the step of actuating the elongate plunger may be applying force 60 in the direction that is substantially parallel to shaft 26 (e.g., FIGS. 1-7). While not being required, it can be advantageous that the following steps occur in the following sequential order: providing, followed by locating, followed by joining, followed by actuating.

In practice, device 10 may be used as follows. Force 60 can be applied to plunger 40 (e.g., by a user's thumb and/or finger(s) or the like) at plunger user end 44, causing it, i.e., incrementally, to go into shaft 26 at the plunger user end and thereby cause plunger ear end 42 to leave shaft 26, and optionally deform resilient bladder 70, i.e., incrementally, from the at-rest position then to the in-ear position, optionally through the insertion position, and then back to the in-ear position, when the force 60 is removed from the plunger. At this point, the device 10 would be located in ear canal 12 in a partially expanded condition to block the ear canal for sound optimization such as noise reduction and/or acoustic enhancement. In particular, the in-ear position is determined by the user's particular ear canal shape and size and is therefore self-fitting or customizable.

Referring to FIGS. 14-17, there is depicted other embodiments of the invention, but in a more traditional ear plug type configuration. Even though traditional, each still is a self-fitting device 10 for location in the ear canal. Each includes a body 20 having a body ear end 22 and an opposite body user end 24 and a body cross-section with a body cross-section width 110. A resilient bladder 70 is joined with the body and the bladder has a wall portion 74 that is deformable from an at-rest position to an in-ear position. The these FIG. 14-17 embodiments, the bladder has a more open configuration than what is taught in FIGS. 1-12. The resilient bladder has a bladder cross-section where the bladder cross-section has a bladder cross-section width 112 that is greater than the body cross-section width 110. The bladder 70 has a variable strength profile in the wall portion 74 of the bladder.

Advantageously, though not required, at least a second (and even a third, fourth or more) resilient bladder 120 may be joined with the body 20 and have a wall portion 124 that is deformable from an at-rest position to an in-ear position. The second resilient bladder can have a second bladder cross-section where the second bladder cross-section has a second bladder cross-section width 122 that is greater than the body cross-section width 110 and is less than the bladder cross-section width 112. The second resilient bladder 120 can be located closer to the body ear end 22 than the resilient bladder 70 is so located.

Without being limited to a particular theory of understanding or noted advantageous features, the following features are discussed. The reduction in the cross-sectional area is converted into additional length of bladder 70 thus reducing the diametrical force exerted on small ear canals, thereby enhancing comfort even for smaller ear canals. The diametrical force can be even further reduced, and comfort enhanced, with the variable strength profile features discussed herein. Also, the diametrical reduction is achieved more conveniently than foam ear plugs and more effectively than for most ear plug types thus increasing the likelihood of proper insertion and more optimal protection, for all size ear canals.

When in use and acoustic enhancement is desired, actuating the plunger optionally reduces the cross-sectional area of the resilient bladder while device 10 is still inserted in the ear canal thus increasing the users hearing ability without requiring that device 10 to be removed. For removal, since the cross-sectional area can be reduced, it breaks the seal with the ear canal prior to removal, for a more comfortable removal. Alternatively, the device 10 can simply be pulled out slowly without having to re-extend bladder 70. Also, with the features of the present invention it is made of sufficiently substantial materials and design so as to allow for multiple uses.

For a discussion of additional optional features for use with the invention, reference is made to assignee's prior filed application, of the same title, and having U.S. Ser. No. 11/799,344 filed Apr. 30, 2007 (aka PCT/IB2008/050922 filed Mar. 13, 2008), and assignee's co-filed application, also with the same title as this application, both of which are incorporated herein by reference.

As various changes could be made in the above constructions and methods, without departing from the scope of the invention, it is intended that all matter contained in the above description and shown in the accompanying drawings shall be interpreted as illustrative and not in a limiting sense.

When introducing elements of the invention or the preferred aspect(s) thereof, the articles "a", "an", "the" and "said" are intended to mean that there are one or more of the elements. The terms "comprising", "including" and "having" are intended to be inclusive and mean that there may be additional elements other than the listed elements.

What is claimed is:

1. A self-fitting device for location in an ear canal, comprising:
   a body having a body ear end, an opposite body user end, and a shaft extending from the ear end to the user end;
   a resilient bladder joined with the body ear end and a chamber defined inside the resilient bladder where the chamber is in communication with the shaft and the resilient bladder has a wall portion and is deformable from an at-rest position to an in-ear position; and,
   an elongate plunger located in the shaft, the elongate plunger having a plunger user end extending out of the shaft and away from the body ear end and an opposite plunger ear end in communication with the resilient bladder, wherein the elongate plunger actuates between the at-rest position and an insertion position to assist the resilient bladder to in being deformed from the at-rest position to the in-ear position; and
   the resilient bladder having a variable strength profile in the wall portion of the bladder.

2. The device of claim 1 wherein the variable strength profile comprises a plurality of relief zones located in an inside portion of the wall portion of the bladder.

3. The device of claim 2 wherein the relief zones comprise grooves located in an inside surface of the wall portion of the bladder.

4. The device of claim 3 wherein the grooves comprise axial grooves.

5. The device of claim 3 wherein the grooves comprise radial grooves.

6. The device of claim 3 wherein the grooves comprise a criss-cross pattern of grooves.

7. The device of claim 2 wherein the relief zones comprise a network of peaks and valleys in the wall portion of the bladder.

8. The device of claim 7 wherein the network comprises an aligned pattern of the peaks and valleys.

9. The device of claim 1 wherein the resilient bladder has a first cross-sectional area in the at-rest position and a second cross-sectional area in the in-ear position, and wherein the first cross-sectional area is greater than the second cross-sectional area.

10. The device of claim 1 wherein the variable strength profile comprises the resilient bladder formed of a first layer overlying a second layer and the first layer having a first durometer and the second layer having a second durometer wherein the first durometer is different than the second durometer.

11. The device of claim 10 wherein the first durometer is greater than the second durometer.

12. A self-fitting device for location in an ear canal, comprising:
   a body having a body ear end, an opposite body user end, and a shaft extending from the ear end to the user end;
   a resilient bladder joined with the body ear end and a chamber defined inside the resilient bladder where the chamber is in communication with the shaft and the resilient bladder has a wall portion and is deformable from an at-rest position to an in-ear position;

the resilient bladder comprising a plurality of relief zones located in an inside portion of the wall portion of the bladder; and, an elongate plunger located in the shaft, the elongate plunger having a plunger user end extending out of the shaft and away from the body ear end and an opposite plunger ear end in communication with the resilient bladder, wherein the elongate plunger actuates between the at-rest position and an insertion position to assist the resilient bladder in being deformed from the at-rest position to the in-ear position, and the resilient bladder has a first cross-sectional area in the at-rest position and a second cross-sectional area in the in-ear position, and wherein the first cross-sectional area is greater than the second cross-sectional area.

13. A self-fitting device for location in an ear canal, comprising:

a body having a body ear end and an opposite body user end and a body cross-section with a body cross-section width;

a resilient bladder joined with the body and having a wall portion that is deformable from an at-rest position to an in-ear position, the resilient bladder also having a bladder cross-section where the bladder cross-section has a bladder cross-section width that is greater than the body cross-section width; and, the resilient bladder having a variable strength profile in the wall portion of the bladder, and wherein the variable strength profile comprises a plurality of relief zones located in an inside portion of the wall portion of the bladder.

14. The device of claim 13 wherein the relief zones comprise a member from the group of axial grooves, radial grooves and a combination of axial and radial grooves, located in an inside surface of the wall portion of the bladder.

15. The device of claim 13 wherein the relief zones comprise a network of peaks and valleys in the wall portion of the bladder.

16. The device of claim 13 wherein the resilient bladder has a first cross-sectional area in the at-rest position and a second cross-sectional area in the in-ear position, and wherein the first cross-sectional area is greater than the second cross-sectional area.

17. The device of claim 13, comprising a second resilient bladder joined with the body and having a wall portion that is deformable from an at-rest position to an in-ear position, the second resilient bladder also having a second bladder cross-section where the second bladder cross-section has a second bladder cross-section width that is greater than the body cross-section width and is less than the bladder cross-sectional width, and the second resilient bladder is located closer to the body ear end than the resilient bladder is so located.

* * * * *